US008350706B2

(12) United States Patent
Wegelin et al.

(10) Patent No.: US 8,350,706 B2
(45) Date of Patent: Jan. 8, 2013

(54) HYGIENE COMPLIANCE MONITORING SYSTEM

(75) Inventors: Jackson W. Wegelin, Stow, OH (US); Todd J. Cartner, Uniontown, OH (US); Chip Curtis, West Dundee, IL (US)

(73) Assignee: GOJO Industries, Inc., Akron, OH (US)

( * ) Notice: Subject to any disclaimer, the term of this patent is extended or adjusted under 35 U.S.C. 154(b) by 423 days.

(21) Appl. No.: 12/494,693

(22) Filed: Jun. 30, 2009

(65) Prior Publication Data

US 2010/0332022 A1 Dec. 30, 2010

(51) Int. Cl.
G08B 23/00 (2006.01)
B67D 51/08 (2006.01)

(52) U.S. Cl. ............ 340/573.1; 340/517; 340/523; 222/52

(58) Field of Classification Search ........ 340/573.1, 340/573.4, 540, 541, 567, 539.1, 539.11, 340/539.12, 517, 523, 526; 4/39, 52, 222, 4/223; 422/26, 28, 123, 124; 700/236, 238; 222/39, 52, 222, 223
See application file for complete search history.

(56) References Cited

U.S. PATENT DOCUMENTS

| | | |
|---|---|---|
| 3,967,478 A | 7/1976 | Guinn |
| 4,606,085 A | 8/1986 | Davies |
| 4,896,144 A | 1/1990 | Bogstad |
| 5,202,666 A | 4/1993 | Knippscheer |
| 5,610,589 A | 3/1997 | Evans et al. |
| 5,670,945 A | 9/1997 | Applonie |
| 5,695,091 A | 12/1997 | Winings et al. |
| 5,771,925 A | 6/1998 | Lewandowski |
| 5,793,653 A | 8/1998 | Segal |
| 5,812,059 A | 9/1998 | Shaw et al. |
| 5,818,617 A | 10/1998 | Shipley |
| 5,900,801 A | 5/1999 | Heagle et al. |
| 5,939,974 A | 8/1999 | Heagle et al. |
| 5,945,910 A | 8/1999 | Gorra |
| 5,952,924 A | 9/1999 | Evans et al. |
| 5,954,069 A | 9/1999 | Foster |
| 6,029,600 A | 2/2000 | Davis |
| 6,031,461 A | 2/2000 | Lynn |
| 6,038,331 A | 3/2000 | Johnson |
| 6,147,607 A | 11/2000 | Lynn |
| 6,206,238 B1 | 3/2001 | Ophardt |
| 6,211,788 B1 | 4/2001 | Lynn et al. |

(Continued)

FOREIGN PATENT DOCUMENTS

WO 03/082351 A2 10/2003
(Continued)

Primary Examiner — Van T. Trieu
(74) Attorney, Agent, or Firm — Renner, Kenner, Greive, Bobak, Taylor & Weber

(57) ABSTRACT

A hygiene compliance monitoring system provides a dispenser that is associated with a data collection unit that collects dispensing events, such as the dispensement of material from the dispenser, which occurs during time segments of a predetermined duration. The hygiene event monitoring system also includes a portable data acquisition unit that is in wireless communication with the data collection unit of the dispenser. As such, when the data acquisition unit is brought within the range of reception of the data collection unit, the hygiene compliance data and time segment information are transmitted to the data acquisition unit and stored at a portable memory unit, which is removable. As such, the hygiene compliance data stored on the portable memory unit can be readily transferred to any desired computing device for analysis and report generation.

20 Claims, 7 Drawing Sheets

U.S. PATENT DOCUMENTS

| | | |
|---|---|---|
| 6,236,317 B1 | 5/2001 | Cohen et al. |
| 6,264,548 B1 * | 7/2001 | Payne et al. .................. 454/157 |
| 6,278,372 B1 | 8/2001 | Velasco, Jr. et al. |
| 6,360,181 B1 | 3/2002 | Gemmell et al. |
| 6,375,038 B1 | 4/2002 | Daansen et al. |
| 6,392,546 B1 | 5/2002 | Smith |
| 6,404,837 B1 | 6/2002 | Thompson et al. |
| 6,426,701 B1 | 7/2002 | Levy et al. |
| 6,536,060 B1 | 3/2003 | Janssen et al. |
| 6,577,240 B2 | 6/2003 | Armstrong |
| 6,707,873 B2 | 3/2004 | Thompson et al. |
| 6,727,818 B1 | 4/2004 | Wildman et al. |
| 6,882,278 B2 | 4/2005 | Winings et al. |
| 6,883,563 B2 | 4/2005 | Smith |
| 6,975,231 B2 | 12/2005 | Lane et al. |
| 7,015,816 B2 | 3/2006 | Wildman et al. |
| 7,163,101 B2 | 1/2007 | Harper |
| 7,242,307 B1 | 7/2007 | LeBlond et al. |
| 7,271,728 B2 | 9/2007 | Taylor |
| 7,285,114 B2 | 10/2007 | Harper |
| 7,286,057 B2 | 10/2007 | Bolling |
| 7,293,645 B2 | 11/2007 | Harper et al. |
| 7,315,245 B2 | 1/2008 | Lynn et al. |
| 2,372,367 A1 | 5/2008 | Lane et al. |
| 7,375,640 B1 | 5/2008 | Plost |
| 7,408,470 B2 | 8/2008 | Wildman et al. |
| 7,411,511 B2 | 8/2008 | Kennish et al. |
| 7,423,533 B1 | 9/2008 | LeBlond et al. |
| 7,425,900 B2 | 9/2008 | Lynn et al. |
| 7,426,491 B1 | 9/2008 | Singer et al. |
| 7,443,305 B2 | 10/2008 | Verdiramo |
| 7,477,148 B2 | 1/2009 | Lynn et al. |
| 7,482,936 B2 | 1/2009 | Bolling |
| 7,542,586 B2 | 6/2009 | Johnson |
| 7,894,936 B2 * | 2/2011 | Walker et al. .................. 700/238 |
| 2002/0082177 A1 | 6/2002 | Tabaac |
| 2007/0229288 A1 | 10/2007 | Ogrin et al. |
| 2007/0257803 A1 | 11/2007 | Munro et al. |
| 2008/0001763 A1 | 1/2008 | Raja et al. |
| 2008/0087719 A1 | 4/2008 | Sahud |
| 2008/0099045 A1 | 5/2008 | Glenn et al. |
| 2008/0100441 A1 | 5/2008 | Prodanovich et al. |
| 2008/0131332 A1 | 6/2008 | Nguyen et al. |
| 2008/0185395 A1 | 8/2008 | Sahud |
| 2008/0246599 A1 | 10/2008 | Hufton et al. |
| 2008/0303658 A1 | 12/2008 | Melker et al. |
| 2009/0045217 A1 | 2/2009 | Bobrowski |
| 2009/0068116 A1 | 3/2009 | Arndt |
| 2009/0084407 A1 | 4/2009 | Glenn et al. |
| 2009/0091458 A1 | 4/2009 | Deutsch |

FOREIGN PATENT DOCUMENTS

| | | |
|---|---|---|
| WO | 2006/135922 A2 | 12/2006 |
| WO | 2007133960 | 11/2007 |

* cited by examiner

HYGIENE COMPLIANCE MONITORING SYSTEM

TECHNICAL FIELD

The present invention generally relates to systems to monitor compliance with hygiene protocols. Particularly, the present invention relates to compliance monitoring systems that utilize a portable data acquisition unit to wirelessly retrieve hygiene compliance data from data collection devices maintained by a dispenser.

BACKGROUND OF THE INVENTION

Recently, the public has become increasingly concerned with disease and its transmission, and as such, there is an increased awareness of the importance of cleansing and hygiene in general. For example, with respect to the transmission of E. coli in the food services industry, the rhinovirus in elementary schools, and nosocomial diseases within healthcare facilities, numerous studies have cited hand hygiene as an effective measure to guard against disease transmission. Moreover, the Center for Disease Control (CDC) has set forth that hand washing and sanitizing is the single most important factor in the prevention of disease and the spread of infection. In response, the health care industry, the food services industry, and the hotel and travel industries have been forced to examine their protocols and procedures to ensure that their personnel are adopting hand cleansing habits that are efficacious in the prevention of disease transmission.

In order to minimize the chance of the transmission of bacteria or viruses by hand washing, full compliance with hand washing hygiene standards must be observed, as the failure of one individual to properly sanitize his or her hands can negate the efforts of others who come in contact with such individual. Thus, to ensure that full compliance occurs, many industries have trained individuals who are charged with overseeing compliance with hygiene standards. Unfortunately, individuals overseeing compliance with hygiene standards typically have other responsibilities, which often interfere with their ability to effectively monitor hygiene compliance. To overcome this, automated systems have been developed that monitor the usage habits of soap dispensers as an aid in the determination of whether compliance with hygiene protocols is being achieved. However, due to the relatively complex nature of these systems, trained individuals are generally needed to administrate and maintain the systems. Additionally, because individuals responsible for overseeing the operation of the compliance monitoring systems are often subject to high turnover, frequent retraining is necessitated, which requires substantial time and expense.

In addition, compliance monitoring systems often utilize wired or wireless computer networks with which to communicate the hygiene data collected from the dispenser to a central computer database. However, integrating the computer network with a plurality of dispensers that may be distributed throughout many rooms and floors of a building results in a highly complex system, which is undesirable. Furthermore, unless the communication network associated with each dispenser was installed at the time of construction of the building or structure maintaining the dispensers, retrofitting a wired computer network for communication to each dispenser is likely cost prohibitive. And while wireless communication networks may be utilized in cases where the dispensers have already been installed, the power requirements needed to power a wireless network transceiver at each dispenser that is capable of transmitting hygiene compliance data to a centrally-located computer system and database would necessitate access to wired power sources, which may be logistically prohibitive.

While other hygiene compliance data collection systems that are easier to install and administrate are available, they utilize remote data logging devices that are not capable of reading data collected from a dispenser at a distance outside of the room where the dispenser is located. That is, such systems require that the data logging device be brought into close proximity of the dispenser before hygiene compliance data can be transferred thereto, which is undesirable when data from a large number of dispensers is being collected. Furthermore, bringing the data logging device in close proximity to the dispenser can be a burden in isolation wards and other areas that require limited patient contact and/or the wearing of a gown and gloves to enter the area. Moreover, such hygiene compliance monitors generally maintain a memory of insufficient size that is overrun when too many hygiene events are recorded and stored.

Thus, current hygiene compliance monitoring systems typically do not offer robust data collection features and are generally too complex to install, administrate, and maintain to be utilized on a large scale in environments where the monitoring and assessment of compliance with hygiene standards is of critical importance and benefit to prevent disease transmission.

Therefore, there is a need for a user-friendly hygiene compliance monitoring system for assessing compliance with predetermined hygiene protocols. In addition, there is a need for a hygiene compliance monitoring system to monitor the use of soap and sanitizer dispensers that collect hygiene usage data in time segments or grouping intervals to ensure that a memory unit maintained thereby is not overrun. Furthermore, there is a need for a hygiene compliance monitoring system that utilizes a portable data acquisition unit that wirelessly retrieves collected hygiene compliance data from a data collection unit associated with a dispenser. There is also a need for a hygiene compliance monitoring system that uses a removable portable memory unit to simplify the transfer of data from the system.

SUMMARY OF THE INVENTION

In light of the foregoing, it is a first aspect of the present invention to provide a hygiene compliance monitor for a dispenser maintaining material to be dispensed, said hygiene compliance monitor comprising a dispenser controller that is coupled to an actuator to initiate the dispensement of material from the dispenser when said actuator is actuated; a data collection unit adapted to be coupled to said dispenser controller, said data collection unit including a data collection memory unit, such that said data collection unit generates at least one time segment of a predetermined duration, said data collection unit associating the number of actuations of said actuator with said time segment in which said actuations occurred; and a data acquisition unit in wireless communication with said data collection unit to receive the associated number of actuations and said time segments therefrom.

It is another aspect of the present invention to provide a hygiene compliance monitor for a dispenser maintaining material to be dispensed, said hygiene compliance monitor comprising a dispenser controller that is coupled to an actuator to initiate the dispensement of material from the dispenser when said actuator is actuated; a data collection unit adapted to be coupled to said dispenser controller, said data collection unit including a data collection memory unit and an internal clock, said data collection unit associating at least one actuation of said actuator with a time stamp generated from said internal clock; and a data acquisition unit in wireless communication with said data collection unit, wherein said data acquisition unit is configured to wirelessly set said clock and is further configured to receive at least one piece of data indicating the associated time stamp information of said at least one actuation.

Yet another aspect of the present invention is to provide a hygiene compliance monitor for a dispenser maintaining material to be dispensed, said hygiene compliance monitor comprising a dispenser controller that is coupled to an actuator to initiate the dispensement of material from the dispenser when said actuator is actuated; a data collection unit adapted to be coupled to said dispenser controller, said data collection unit including a data collection memory unit, said data collection unit collecting data from at least one actuation of said actuator; and a data acquisition unit in wireless communication with said data collection unit, wherein said data acquisition unit is configured to wirelessly program said data collection unit with location identifying information and is further configured to receive the collected data stored at said data collection unit.

It is a further aspect of the present invention to provide a hygiene compliance system for a plurality of dispensers maintaining material to be dispensed, said hygiene compliance system comprising a plurality of hand hygiene compliance units, wherein each of said hand hygiene compliance units includes a dispenser controller coupled to an actuator to initiate the dispensement of material from a dispenser within the plurality of dispensers when said actuator is actuated, and a data collection unit adapted to be coupled to said dispenser controller, said data collection unit including a data collection memory unit, said data collection unit collecting data from at least one actuation of said actuator; and a data acquisition unit in wireless communication with said plurality of data collection units within said plurality of hand hygiene compliance units, wherein said data acquisition unit is configured to wirelessly receive the collected data stored at said data collection unit within at least two of said hand hygiene compliance units within said plurality of said hand hygiene compliance units, wherein said two hand hygiene compliance units are located within a predetermined proximity to one another, and further wherein the data from said at least two hand hygiene compliance units is wirelessly received nearly simultaneously.

Yet another aspect of the present invention is to provide a method of hygiene compliance monitoring comprising providing a data collection unit maintained by a dispenser, said dispenser including an actuator to initiate the dispensement of material from a refill container; wherein said data collection unit generates a plurality of time segments of a predetermined duration at said data collection unit, monitors the engagement of said actuator, associates the number of engagements of said actuator with the time segment in which said engagements occurred, and stores the number of engagements and associated time segments at said data collection unit; providing a data acquisition unit having a portable memory unit, said data acquisition unit configured to wirelessly communicate with said data collection unit; and further wherein said data collection unit transfers the number of engagements and associated time segments to said portable memory unit.

BRIEF DESCRIPTION OF THE DRAWINGS

These and other features and advantages of the present invention will become better understood with regard to the following description, appended claims, and accompanying drawings where:

BEST MODE FOR CARRYING OUT THE INVENTION

It is known in the art that hand hygiene compliance is typically calculated as the ratio of the number of actual hand hygiene events to the number of hand hygiene events that should have occurred. Thus, to facilitate the determination of whether hygiene compliance standards are being followed, the system of the present invention generally monitors hand hygiene events that have actually occurred, which may be used in conjunction with data related to the number of hand hygiene events that should have occurred to establish a measure of hand hygiene compliance. Furthermore, the terms "hygiene compliance data" and "hygiene event data" may be used interchangeably throughout the following discussion.

Figure 1:
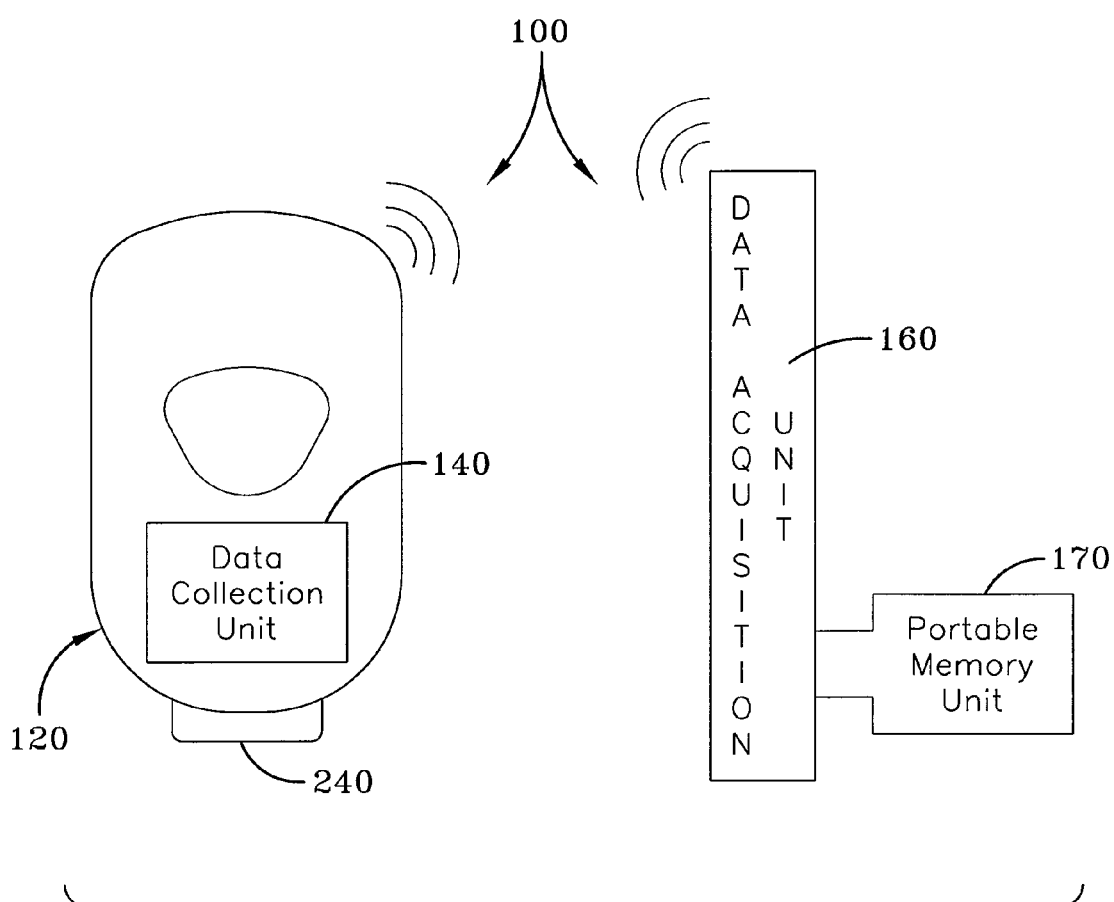
FIG. 1 is a block diagram of a hygiene compliance monitoring system that provides a data collection unit maintained at a dispenser, which transfers collected hygiene compliance data to a remote data acquisition unit in accordance with the concepts of the present invention.

A certain embodiment of a hygiene compliance monitoring system is generally referred to by the numeral 100, as shown in FIG. 1 of the drawings. The hygiene compliance monitoring system 100 is generally used in connection with a dispenser 120, such as a dispenser that dispenses material, such as soap, sanitizer, moisturizer, and the like. However, it should be appreciated that the hygiene compliance monitoring system 100 may be used in association with dispensers used to dispense any suitable material or item. In order to carry out the functions of the hygiene compliance monitoring system 100, a data collection unit (DCU) 140 is associated with the dispenser 120 to collect hygiene data or events, which may include the number of shots of soap dispensed by the dispenser 120 or the number of hand hygiene events occurring at the dispenser 120, such that a hand hygiene event may include one or more shots of soap dispensed by the dispenser 120 within a certain dwell time, or period of time, such as three seconds for example, as it is known that on occasion a user will activate the dispenser 120 to provide two or more shots of soap in a consecutive fashion during a single hand hygiene event. It should also be appreciated that any other desired data associated with the operation of the dispenser 120 can be collected by the DCU 140, as well. Moreover, as later discussed, the number of shots of soap dispensed by the dispenser 120 may be grouped into time segments or grouping intervals of a predetermined duration when recorded by the DCU 140, which ensures that the collected data does not exceed the memory capacity of the data collection unit 140.

The data acquired by the data collection unit 140 is then wirelessly communicated to a portable data acquisition unit (DAU) 160 when brought in proximity thereto. As such, the data is stored on the DAU 160 in a manner so that it can be later analyzed via the DAU 160, or the data may be stored on the DAU 160 in such a manner, such that it can be later transferred to another device, such as a computing device, for analysis. However, in certain preferred embodiments of the invention, once the hygiene compliance data is collected by the data acquisition unit 160, it is stored at a portable memory unit 170 that is removably attached thereto. In one aspect, the portable memory unit 170 may comprise a USB memory unit, a SECURE DIGITAL (SD) memory unit, a COMPACT FLASH (CF) memory unit, flash memory, solid state hard drive, standard hard drive, removable hard drive, or any other suitable memory unit for transferring data from the DAU 160 to a compatible computing device for analysis of the data. Furthermore, the portable memory unit 170 may then be operably coupled to any compatible computing device where the stored hygiene compliance data may be processed for the generation of reports, or it may be transferred over a computer network, such as the Internet, to another computing device or network for analysis. Thus, the hygiene compliance system 100 provides a convenient and user-friendly system in which to implement and use in order to collect data relating to the use of the dispenser 120, so as to assist in determining whether predetermined hygiene standards and protocols are being met.

Figure 2:
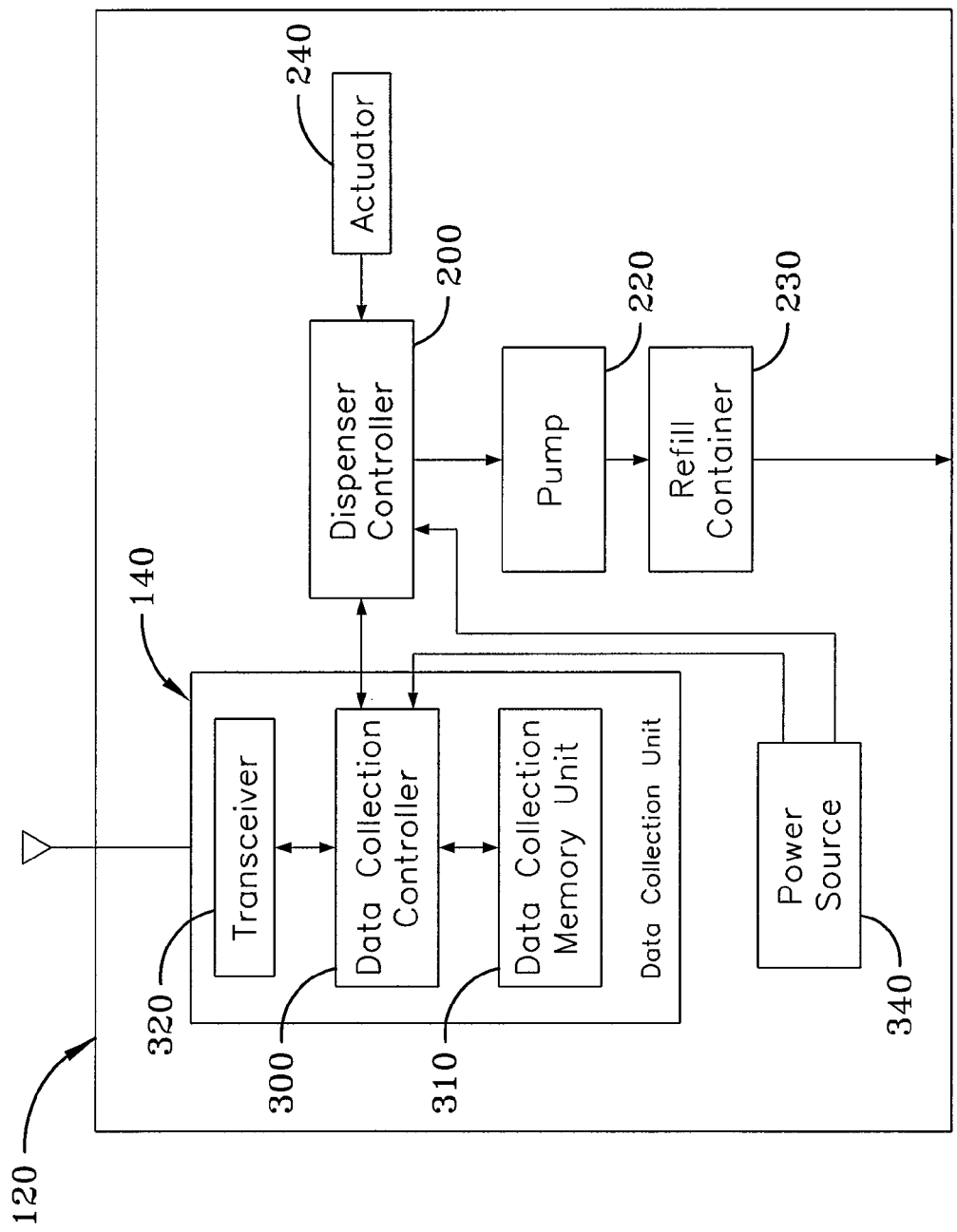
FIG. 2 is a block diagram of the data collection unit associated with the dispenser in accordance with the concepts of the present invention.

Continuing to FIG. 2, in various embodiments of the invention, the dispenser 120 maintains a dispenser controller 200, which controls a pump 220 connected thereto. A refill container 230 is operatively coupled to the pump 220 and may maintain any desired material, such as soap, sanitizer, moisturizer, or the like. Also coupled to the controller 200 is an actuator 240 that when engaged or otherwise actuated, commands the dispenser controller 200 to actuate the pump 220, so as to dispense material from the refill container 230. In one aspect, the actuator 240 may comprise a proximity sensor or other device that is actuated upon the detection of the presence of a user's hand. However, in further aspects of the invention, the actuator may be coupled to a manual push bar wherein material is dispensed onto the users hand when the user manually activates the push bar.

The dispenser 120 also includes the data collection unit 140, which is coupled to the dispenser controller 200. The data collection unit 140 may be implemented in hardware, software, or a combination of both. In one aspect, the data collection unit 140 may be integral with the dispenser controller 200 or maintained separately therefrom, as shown in FIG. 2. In yet another aspect, the data collection unit 140 may be provided as a separate component that provides a compatible interface for communicating with the dispenser 120 to allow the data collection unit 140 to be retrofit with the dispenser 120. Thus, the features provided by the hygiene compliance monitoring system 100 may be subsequently added or retrofitted to previously-installed dispensers 120 that lack such features.

The data collection unit 140 maintains a data collection controller 300, which is coupled to the dispenser controller 200 of the dispenser 100. The data collection controller 300 includes the necessary hardware, software, or combination of both needed to carry out the functions to be discussed. Specifically, the data collection controller 300 maintains an event count or event count value, which is incremented based on the number of actuator 240 engagements that have been made to dispense material from the dispenser 120 during a particular grouping interval or time segment. The event count or event count value may be based on the actual number of dispenses from the dispenser, or the number of hand hygiene events, which may include a number of dispenses from the dispenser in a predetermined period of time, or both the actual number of dispenses and the number of hand hygiene events. For each current grouping interval or time segment, the data collection controller 300 maintains an event count value that in certain embodiments is incremented each time the actuator 240 is engaged and in other embodiments is incremented each time a hand hygiene event occurs. And as such, it is the combination of the event count value and associated grouping interval which comprises hygiene compliance data.

Coupled to the data collection controller 300 is a data collection memory unit 310 that stores data collected by the data collection unit 140. Specifically, the data collection memory unit 310 of the data collection unit 140 is configured such that the memory available for storing data is divided into time segments or grouping intervals of a predetermined duration. As such, once the duration of the time segments has been set via the data acquisition unit 160 in a manner to be discussed, the number of actuator 240 engagements executed at the dispenser 120 or hand hygiene events that occur during each reoccurring time segment or grouping interval are recorded and stored at the data collection memory unit 310. In addition, the data collection unit 140 identifies the start and stop time of the time segment or grouping interval, which may include the day, year, hour, and minute at regular time intervals common across multiple data collection units 140. It should be appreciated that a time segment or grouping interval in which there has not been any actuator engagements may be omitted by the data collection unit 140, such that it is not stored at the data collection memory unit 310 to conserve memory capacity.

In addition, by setting the durational size of the time segment or grouping interval that is used to collect hygiene event data at the data collection unit 140, the total number of grouping intervals or time segments that can be stored at the memory unit 310 are determined to ensure that the data collection memory unit 310 is not overrun. Furthermore, the time segments or grouping intervals allow the maximum period of time between downloading of data from the data collection memory unit 310 to be predetermined, for example, the time segment or grouping interval can be designed or configured based on the assumption that the data collection memory unit 310 will be checked every 90 days, or any other period of time. Thus, setting a five-minute time segment at the data collection unit 140 results in the generation of 288 time segments over a 24-hour time period. However, when the data collection unit 140 is set to a time segment or grouping interval of 60 minutes, 24 time segments are generated over a 24-hour time period. Thus, by increasing the duration of the time segment or grouping interval, fewer time segments or grouping intervals are generated and stored. However, when the number of time segments or grouping intervals is decreased, less temporal resolution is provided, and as such, the ability to identify the time frame when the actuator 240 has been engaged to dispense material from the dispenser 120 is diminished. For example, in the case of the 60-minute time segment, only the total number of shots dispensed or hand hygiene events during each hour is recorded. Whereas in the case of a five-minute time segment, the total number of shots dispensed or hand hygiene events every five minutes is recorded. Thus every hour, 12 time segments or grouping intervals are generated, with each segment or interval being associated with the number of actuator 240 engagements that have been initiated at the dispenser 120. Thus, as the number of time segments or grouping intervals is increased, the greater the precision that is provided when determining when the engagements of the actuator have been made. For example, one useful grouping period or time interval may be established by the start and stop time of each shift.

In yet another aspect, the data collection memory unit 310 may be configured such that each actuator 240 engagement is recorded individually, and when the quantity of data reaches a predetermined level, the data collection unit 140 organizes the collected actuator 240 engagements in accordance with time segments or grouping intervals of a desired duration, as discussed above. By organizing the collected dispensing events into time segments of a predetermined duration, storage space at the data collection memory unit 310 is more precisely managed, so as to conserve memory.

Continuing, the memory unit 310 may preferably comprise non-volatile memory, such that hygiene compliance data collected and stored at the data collection unit 310 is not erased if power to the data collection unit 140 is lost. Data acquired by the data collection unit 140 is stored at the data collection memory unit 310 and is wirelessly transmitted to the portable data acquisition unit 160 via a transceiver 320, such as an RF (radio frequency) or IR (infrared) transceiver, which is coupled to the data collection controller 300. The data collection unit 140, as well as the components of the dispenser 100, is powered by a power source 340, which may comprise a portable power source, such as a battery, or may comprise a mains power source that is plugged into a wall outlet. Alternatively, the data collection unit 140 may provide its own power source, such as a rechargeable or replaceable battery, independently from that of the dispenser 120.

In a further aspect, the data collection unit 140 may be configured to enter a low-power mode during periods when the dispenser 120 is not dispensing any material and/or in which it is not actively monitoring hygiene compliance. And correspondingly, the data collection unit 140 is fully activated or otherwise powered when the data acquisition unit 160 receives a wireless communication signal from the data acquisition unit 160. As such, the data collection unit 140 is able to conserve power at the power source 340 during those periods of time in which it is not actively collecting hygiene compliance data. In another aspect, the system 100 may be configured whereby the DAU 160 includes one or more magnets, and the dispenser 120 includes a hall or reed switch. And as such, when the magnets of the DAU 160 are brought into proximity of the hall or reed switch or there against, the dispenser 120 and the data collection unit 310 are activated, so as to enable the transmission of data therebetween.

The data collection unit 140 is also configured to maintain a dispenser identification code that uniquely identifies the dispenser 120. In one aspect, the dispenser identification code may comprise a data word having eight data fields of 16-bits each, although any other code format may be used. Furthermore, the dispenser identification code maintained by the data collection unit 140 may be defined or formatted so that it identifies the specific location of the dispenser 120 to which it is associated. For example, the dispenser identification code may include a room number, such as 204, in combination with a letter code, such as: S=sink; RB=right bed; and LB=left bed, to identify the specific area of the room where the dispenser 120 is located. For example, the dispenser identification "204-RB" indicates that the particular dispenser 120 is located in room 204 at a point proximate to the right bed maintained therein. Thus, the dispenser identification code allows users of the data acquisition unit 160 to easily locate a dispenser by entering the dispenser identification code via the data acquisition unit 160 in a manner to be discussed, so as to initiate the retrieval of hygiene compliance data collected by the data collection unit 140. In addition, the dispenser identification code may be encrypted so that the location data contained by the dispenser identification code is revealed only upon its decryption by the application of a correct decryption key.

Figure 3:
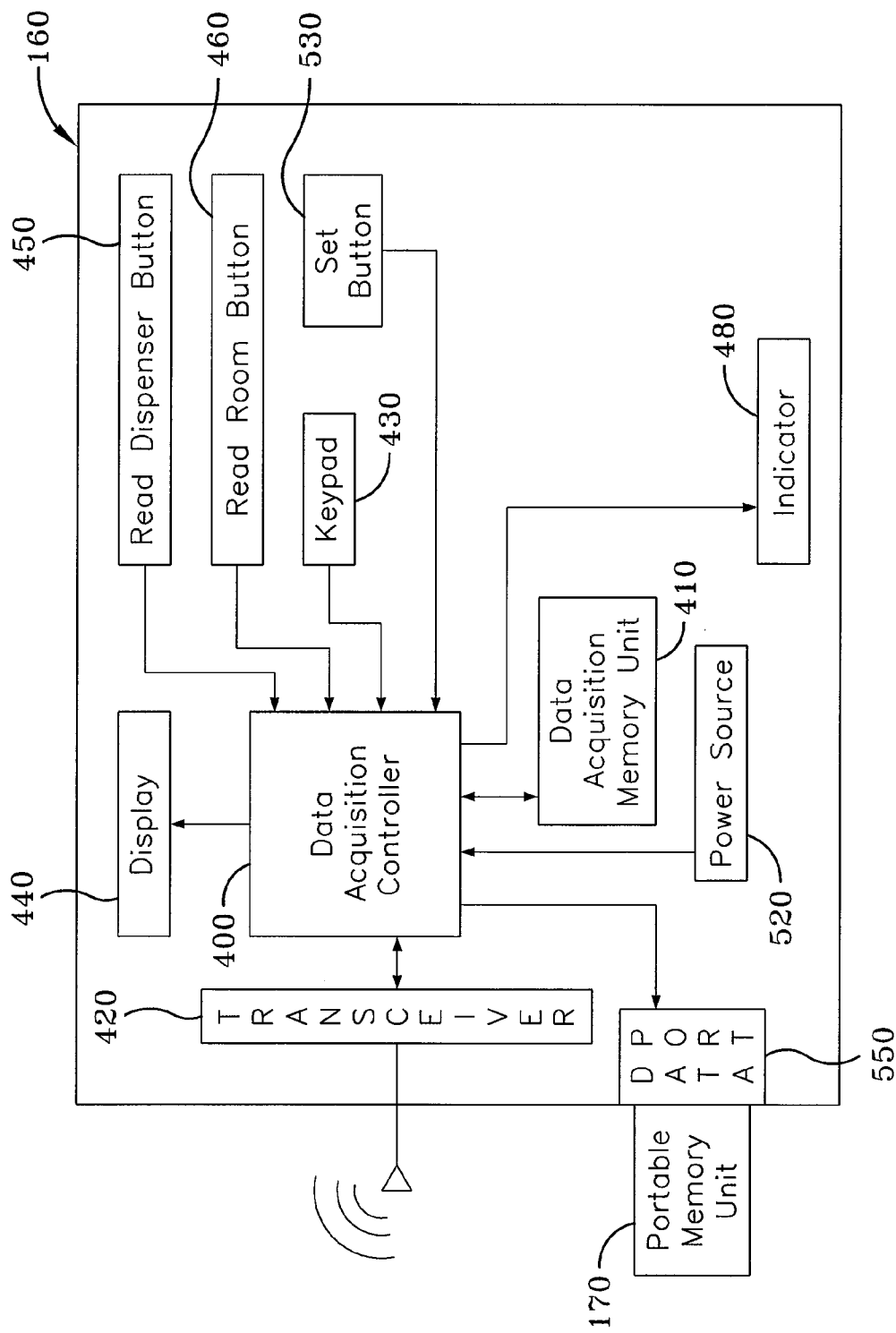
FIG. 3 is a block diagram of the data acquisition unit used to wirelessly retrieve hygiene compliance data from the data collection unit of the dispenser in accordance with the concepts of the present invention.

Continuing to FIG. 3, the portable data acquisition unit 160, which acquires the collected hygiene data from the data collection unit 140, comprises a data acquisition controller 400 that includes the necessary hardware, software, or combination of both needed to provide the functions to be discussed. In one aspect, the data acquisition controller 400 also maintains an internal clock to track the current time and day. In one aspect, the internal clock may be set via the DAU 160 or a rapid interrupter for example. The internal clock may also function such that time is traced in negative relation to the current time. For example, the clock may be used to timestamp data, such that when data is transmitted, the timestamp indicates the data was collected 1,500 minutes prior to the time of transmission of the data. Thus, the system is able to assign the proper time of the time stamp based upon subtraction from the current time. As such, time stamping the data in this manner makes it unnecessary to set the initial time of the internal clock of the data acquisition controller 400.

Also coupled to the data acquisition controller 400 is a data acquisition memory unit 410 that may comprise volatile memory, non-volatile memory, or a combination of both, which is used to carry out various functions to be discussed. It is also contemplated that the data acquisition unit 160 is configured to maintain a database at the data acquisition memory unit 410 of dispenser identification codes that are associated with each dispenser 120, as previously discussed. In addition, the database may also be configured to associate one or more dispenser identification codes with a room identification code that identifies the particular room in which the dispensers 120 associated with the dispenser identification code are located. Thus, by identifying the room identification code, each dispenser that is installed therein can also be identified. It is also foreseen that the dispensers 120 can be associated with any other suitable ID code, such as an ID code indicating the floor, ward, building, or any other designator desired by the user.

To enable the data acquisition unit 160 to wirelessly communicate with the transceiver 320 of the data collection unit 140 so as to receive hygiene compliance data therefrom, a transceiver 420, such as an RF (radio frequency), IR (infrared), or ultrasound transceiver, is coupled to the data acquisition controller 400. Alternatively, however, it should be appreciated that the transceiver 320 of the data collection unit 140 may be replaced by a transmitter, and the transceiver 420 used by the data collection unit 140 of the data acquisition unit 160 may be replaced with a receiver. In one aspect, the wireless transmission of the hygiene compliance data may be encrypted to prevent unauthorized access.

Also coupled to the data acquisition controller 400 is a keypad 430 that allows the user to enter information and commands into the data acquisition unit 160. For example, the keypad 430 may comprise a combination of numeric and/or alphanumeric keys that allow a user to enter various dispenser identification codes or room identification codes to initiate commands at the data acquisition unit 160 and at the data collection unit 140, in a manner to be discussed. In addition, the keypad 430 may be used to enter commands to initiate and control various functions provided by the system 100. Other means of manipulating the data or controlling various functions provided by the data acquisition unit 160 are also foreseen, including the use of a touch screen, thumb wheel, as well as any other system for data entry or interaction with the data acquisition unit 160.

In addition, the data acquisition unit 160 includes a display 440 which may comprise an LCD (liquid crystal display) display or the like and which allows the user to view the various commands and identification codes entered into the data acquisition unit 160. In addition, the display 440 may also provide feedback with respect to communication progress, as well as communication success or failure with the data collection unit 140. In addition, the display 440 may be configured to allow the user to view the various hygiene event data or summaries of that data that have been collected by the data collection unit 140 maintained by the dispenser 120, as well as any other information.

In certain embodiments of the invention, the portable data acquisition unit 160 also includes a read dispenser button 450 and a read room button 460 that are coupled to the data acquisition controller 400. Thus, when the read dispenser button 450 is actuated, the keypad 430 is used to enter a dispenser identification code of a desired dispenser 120 from which to acquire data. Once the dispenser identification code is entered, the data acquisition unit 160 activates the transceiver 420 and sends suitable communication signals to the associated data collection unit 140 to wirelessly retrieve hygiene event data that has been collected thereby.

Additionally, when the read room button 460 is actuated, the user enters a room identification code, which is associated with a specific room or area in which one or more specific dispensers 120 are located, via the keypad 430. A listing of dispenser identification codes associated with the entered room identification code, which is maintained at a database provided by the data acquisition memory unit 410, is presented upon the display 440, whereupon the desired dispenser identification codes for which event data is desired are selected by the user via the keypad 430. Next, the hygiene event data collected at the data collection unit 140 of the selected dispensers 120 are wirelessly transmitted to the data acquisition unit 160.

It should be appreciated that the examples provided for the read function are not limiting and that other embodiments may allow for the read function to occur in alternative ways. For example, the read room button 460 may automatically read all dispensers 120 within transmission range. In other embodiments, there may be merely a single read button, which can be preset to read the closest dispenser 120 or the closest room. The DAU 160 may prompt the user to select groupings from a drop down menu, such as a certain ward or wing. Additionally, the DAU 160 may also automatically prompt the user to follow the same pattern of reading dispensers 120 as previous read attempts, for example "Room 200 complete. Read Room 201?"

Furthermore, it should be appreciated that the read dispenser button 450 and the read room button 460 may be depressed in a predetermined sequence to enable one or more operating modes, including a read-new mode in which newly-collected event data, which has been obtained by the data collection unit 140 since the last data transfer or interrogation, is retrieved by the data acquisition unit; a read-all mode in which all compliance data collected by the data collection unit 140 is transferred to the data acquisition unit 160; and a read/erase mode in which all data collected by the data collection unit 140 is transferred to the data acquisition unit 160 and then subsequently erased from the data collection memory unit 310.

The data acquisition unit 160 also includes an indicator 480, which may provide an audible or visual indication of various states of the data acquisition unit 160 and/or the data collection unit 140. For example, the indicator 480 may provide an indication that the wireless transmission of hygiene compliance data from the data collection unit 140 of the dispenser 120 and to the data acquisition unit 160 is complete. In another aspect, when an error occurs in the wireless transmission of hygiene compliance data between the dispenser 120 and the data acquisition unit 160, the indicator and/or display 440 provides a prompt to indicate that the hygiene compliance data needs to be re-sent or that the user needs to move the data acquisition unit 160 into the wireless communication range of the data collection unit 140.

Continuing, because the data acquisition unit 160 is configured primarily as a portable device, it is powered by a portable power source 520, such as a battery, super capacitor, fuel cell, or the like. However, it should be appreciated that the data acquisition unit 160 may be alternatively powered by any suitable power source, such as a wall outlet.

In addition, in certain embodiments of the invention, to set various parameters associated with the data collection unit 140 and the data acquisition unit 160, a set button 530 is provided by the data acquisition unit 160. The set button 530 is configured such that when depressed in a predetermined sequence, different parameter setting modes are entered. For example, when a grouping interval setting mode is entered, the time period for each time segment or grouping interval that is used by the data collection unit 140 is permitted to be entered using the keypad 430. Additionally, a date and time setting mode may be entered to set the date and time that is used and updated by the data collection unit 140 and by the data acquisition unit 160. The portable data acquisition unit 160 is used to set various parameters associated with the operation of the data collection unit 140. Furthermore, the data collection unit 140 and the data acquisition unit 160 may be configured such that the data acquisition unit 160 sets the date and time of the data collection unit 140 each time the data acquisition unit 160 communicates with the data collection unit 140. In addition, a dwell time setting mode may be entered, whereupon the data acquisition unit 160 sets the dwell time, which is the amount of time that must expire before successive shot dispensements or other successive hygiene events are treated as separate hygiene events by the data collection unit 140. In one aspect, the data acquisition unit 160 may be configured to set the dwell time of the data collection unit 140 to a default dwell time of about 3 seconds. It should be appreciated that access to the various modes entered by depressing the set button 530 may be restricted by password protection, and as such, a specific password is required before specific parameter setting modes can be entered. This prevents unauthorized individuals from setting parameters at the data collection unit 140 and the data acquisition unit 160 in an attempt to corrupt the hygiene compliance data being collected by the system 100.

Furthermore, the set button 530 may be utilized when the hygiene compliance monitoring system 100 is initially placed into operation, whereby the data acquisition unit 160 is placed into an initialization mode by the depression of the set button 530 in a predetermined sequence. Once the initialization mode is entered at the data collection unit 140, the data acquisition unit 160 is used to initialize or set up the "generic" or unprogrammed data collection unit 140 of each dispenser 120, whereby the clock maintained by the data collection controller 300 is set, and whereby the data acquisition unit 160 assigns a dispenser identification code to the data collection unit 140 associated with the dispenser 120. In addition, the data acquisition unit 160 may also enter the grouping interval/time segment setting mode as part of the initialization mode to set the duration of the grouping interval or time segment utilized by the data collection unit 140 to a predetermined default value, such as five minutes, for example.

After data is collected by the DAU 160, the data may be transferred to a computing device for processing and/or analysis. In certain embodiments the data may be processed or analyzed, and reports may be generated from software installed directly on the computing device. In other embodiments, the data may further be transferred from the computing device to another network that may be administered by a third party, such as the vendor providing the hand hygiene compliance system for processing, analysis or reporting. It is foreseen that the processing, analysis or reporting of the data collected from the system may be customized to the user's preferences to provide the user with information that may allow them to improve hand hygiene compliance within their facility.

Thus, in summary of a preferred embodiment of the invention, after the data collection unit 140 of each of the dispensers 120 has been initialized, the dispenser 120 is placed into operation. As such, the data collection unit 140 monitors the actuator 240, such that each successive actuator 240 engagement results in the dispensements of a shot of material from the refill container 230 of a predetermined size. Thus, the data collection unit 140 identifies the dispensements of each shot of material by either monitoring the engagement of the actuator 240 or the actuation of the pump 220. The hygiene data may include the number of actuator 240 engagements, the number of individual shots or dispenses of material from the refill container 230 that are initiated at the dispenser 120 by the actuation of the actuator 240, and/or the number of hand hygiene events occurring at the dispenser 120. The collected hygiene data identifying the number of shots or actuator 240 engagements from the refill container 230 are stored at the data collection memory unit 310 until they are retrieved by the portable data acquisition unit 160. Once it is desired to wirelessly retrieve the hygiene compliance data from the dispensers 120, a read button, such as either the read dispenser button 450 or the read room button 460 of the data acquisition unit 160 is depressed, whereupon the hygiene compliance data associated with the selected room or dispenser is transmitted to the data acquisition unit 160 and stored at the portable memory unit 170.

Figure 4:
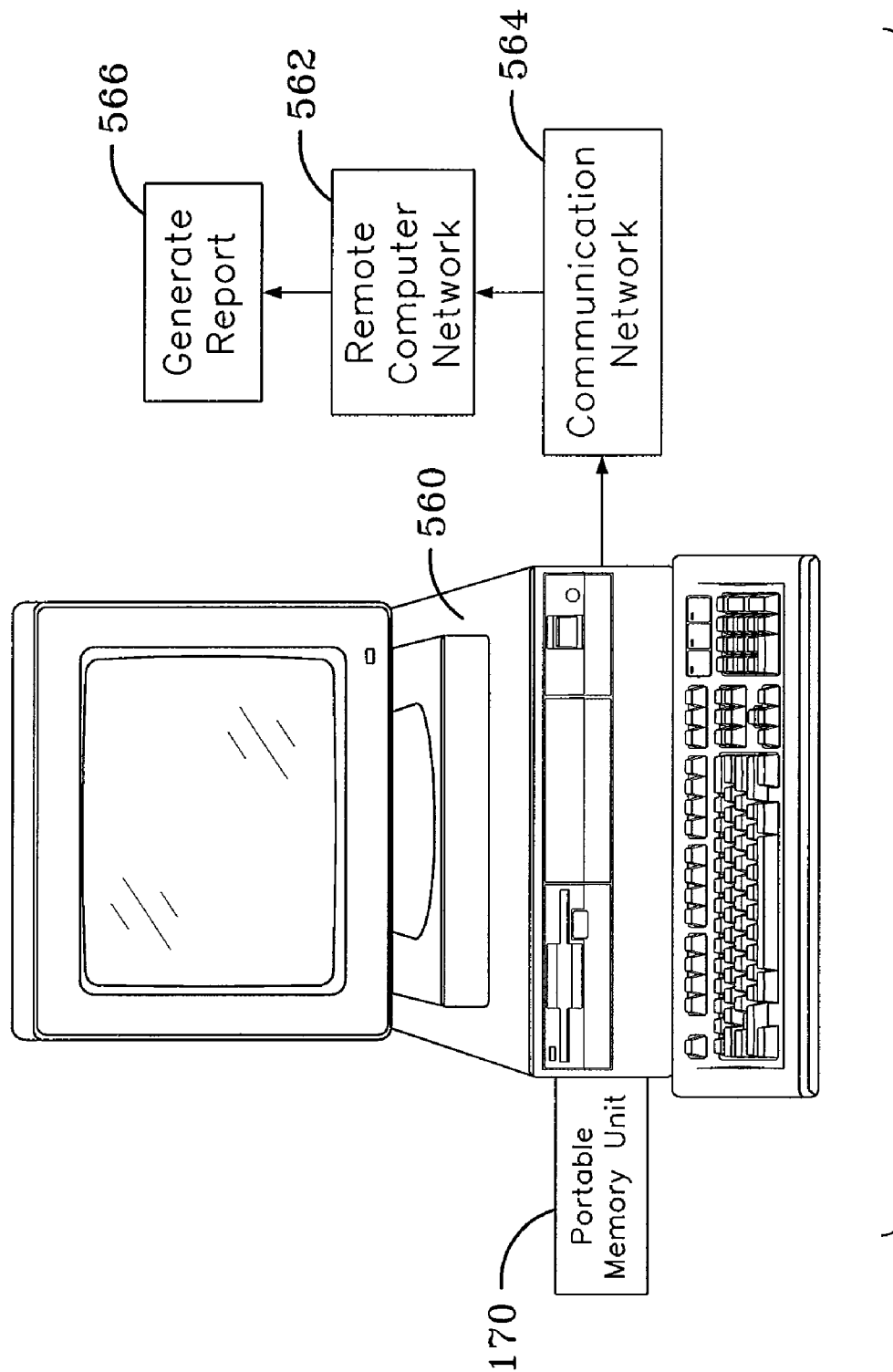
FIG. 4 is a block diagram showing a computer network used to transfer hygiene compliance data from a portable memory unit that is removably maintained by the data acquisition unit to generate reports therefrom in accordance with the concepts of the present invention.

Once the hygiene data from one or more dispensers 120 has been wirelessly acquired from the data collection unit 140 via the data acquisition unit 160, it is stored at the portable memory unit 170 that is removably coupled to the data acquisition controller 400 via a data port 550. Thus, the portable memory unit 170 may be removed from the data acquisition unit 160 and interfaced with any suitable general-purpose or application-specific remote computing device 560, such as a personal computer, as shown in FIG. 4. That is, the hygiene compliance data that is collected from the data acquisition units 140 of each of the dispensers 120 is wirelessly transmitted to the portable data acquisition unit 160.

Once received by the data acquisition unit 160, the hygiene compliance data is stored at the portable memory unit 170, which is then removed and installed at the remote computing device 560 that is in communication with a remote computer system or network 562, such as a remote distributor computer or network. It should be appreciated that the remote computer network 562 may comprise one or more computers that are networked via the Internet, a LAN (local area network), a WAN (wide area network), or any other suitable communication network 564, using a wired or wireless computer network interface. Once the hygiene event data is received at the remote computer network 562, the compliance data is analyzed to generate reports 566.

Thus, a customer that utilizes the hygiene compliance monitoring system 100 may collect hygiene event data from a plurality of dispensers 120 via the data collection units 140. And as users of the system 100 move the data acquisition unit 160 into the communication range of the data collection unit 140 of each dispenser 120, hygiene compliance data is wirelessly transferred to the portable memory unit 170 of the data acquisition unit 160. The portable memory unit 170 is then removed from the data acquisition unit 160 and inserted into the computing device 560. The compliance data may be transferred to a software program installed on the computing device 560 for analysis, or the event data may be transferred to the remote computer network 562, which may be maintained by a third party such as the vendor of the hygiene compliance monitoring system 100. The software system on the computing device 560 or the remote computer network 562 processes and analyzes the data so as to generate meaningful reports 566 that summarize trends associated with the usage of the customer's dispensers 120.

It should also be appreciated that in lieu of the portable memory unit 170, the data acquisition unit 160 may be configured such that the transceiver 420 is enabled to wirelessly transfer hygiene compliance data to the remote computing device 560 as well. It is foreseen that the DAU 160 can also send a dataset to the portable memory unit 170 via a direct connection if the quantity of data is too large to upload via the Internet or other network connection.

Figure 5A:
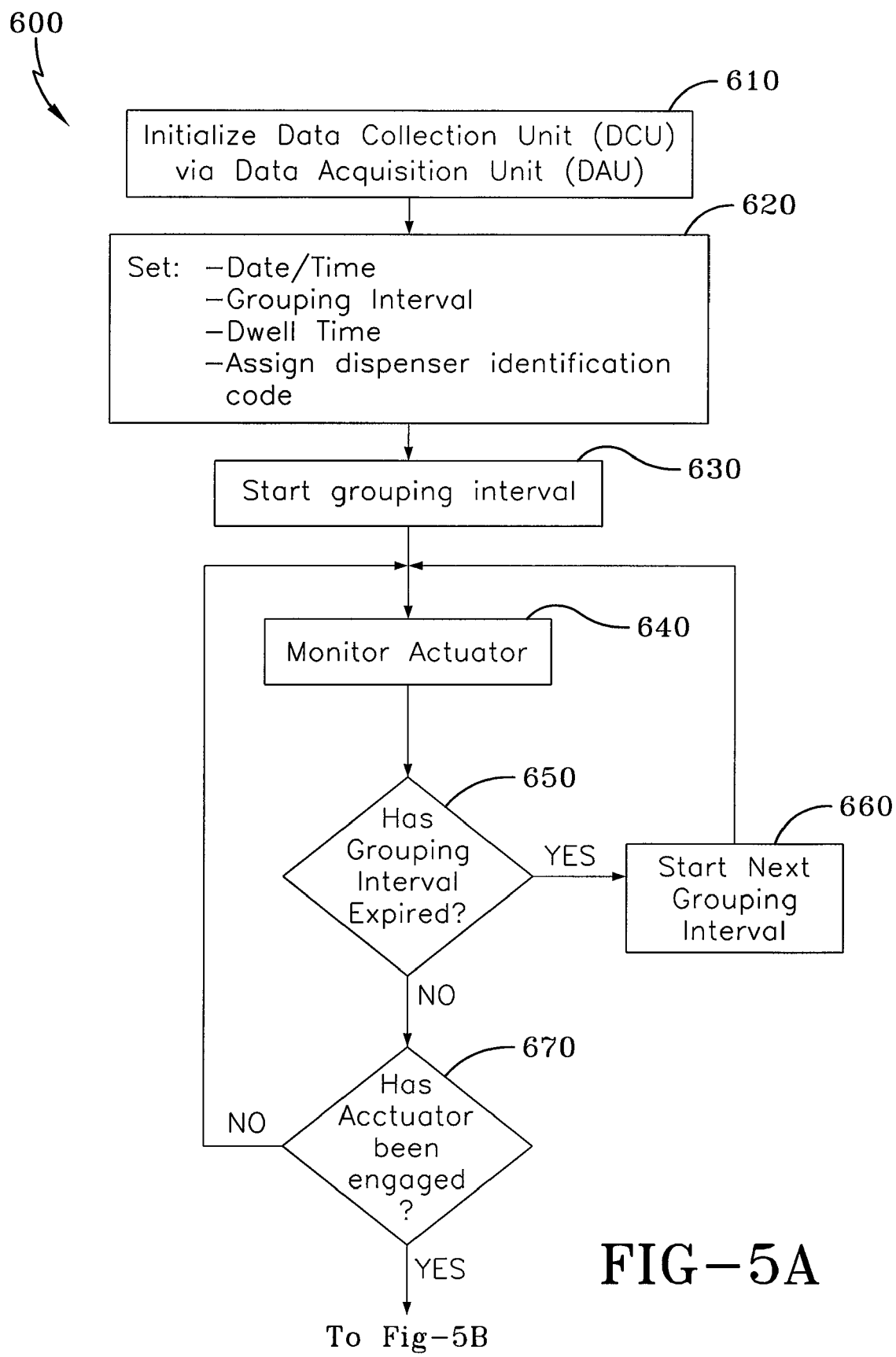
FIGS. 5A-B show a flow diagram of the operational steps taken by the hygiene compliance monitoring system to collect hygiene compliance data at one or more dispensers in accordance with the concepts of the present invention.
Figure 5B:
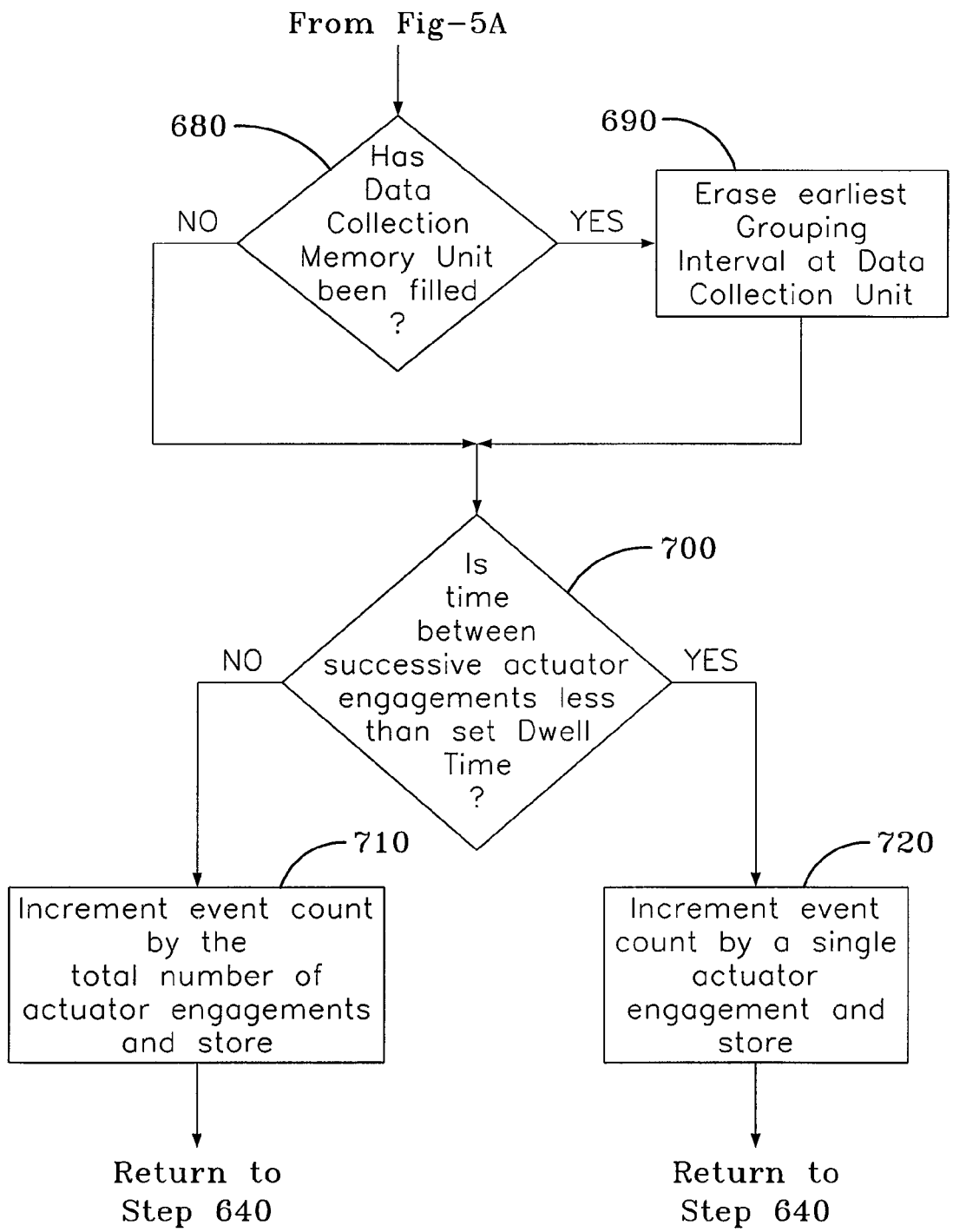

Thus, with the structural components of the hygiene event monitoring system 100 set forth, the operational steps, generally referred to by the numeral 600, as shown in FIGS. 5A-B, that are taken by the system 100 to collect hygiene event data at the dispenser 120 are presented below. Initially, at step 610, the "generic" data collection unit 140 of the dispenser 120 is placed into an initialization mode by depressing the set button 530 in a predetermined sequence at the data acquisition unit 160. During the initialization of the data collection unit 140 at step 620, the date and time, the duration of the grouping interval or time segment, and the dwell time are set at the data collection unit 140. In addition, at step 620, the data acquisition unit 160 assigns a unique dispenser identification code to the data collection unit 140 before continuing to step 630. At step 630, the process 600 initiates the start of the grouping interval and is assigned the current date and time upon the depression of the set button 530 in a predetermined sequence. Somewhat simultaneously with step 630, step 640 is performed, whereupon the data collection unit 140 begins monitoring the dispenser actuator 240. During the span of the grouping interval, step 640 will accumulate both the number of actuations or engagements of the actuator 240 and the number of hand hygiene events that occur during the dwell time. Continuing to step 650, the process determines whether the current grouping interval has expired. If the current grouping interval has expired, the process continues to step 660, where the data collection unit 140 initiates the next grouping interval while identifying its start time. However, if the current grouping interval has not expired, then the process continues to step 670, where the process determines whether the actuator 240 has been engaged.

If at step 670 the actuator 240 has not been engaged, then the process returns to step 640, where the monitoring of the actuator 240 is resumed. However, if the actuator 240 has been engaged, then the process continues to step 680, where the process determines whether the data collection memory unit 310 is filled. If the process determines that the data collection memory unit 310 has been filled, the process continues to step 690, where the grouping intervals stored the earliest in time at the data collection memory unit 310 are erased to create space for the currently-collected hygiene compliance data. As such, the data collection memory unit 310 utilizes a FIFO (First-In First-Out) memory management scheme to make memory space available to currently-collected hygiene compliance data, and as a result, the data collection memory unit 310 is prevented from running out of memory. After the completion of step 690, and if it is determined that the data collection memory unit 140 is not filled at step 680, the process continues to step 700.

At step 700, the process determines whether the time between successive actuator 240 engagements is less than the set dwell time. If the period of time that has elapsed between successive actuator 240 engagements is not less than or equal to the preset dwell time period, then the process continues to step 710, where the event count associated with the current grouping interval is incremented by the total number of actuator 240 engagements and stored at the data collection memory unit 310. However, if the period of time that has elapsed between successive actuator 240 engagements is less than or equal to the preset dwell time period, then the process continues to step 720. At step 720, the event count associated with the current grouping interval is incremented by each detected actuator engagement. After the completion of steps 710 and 720, the process returns to step 640.

Figure 6:
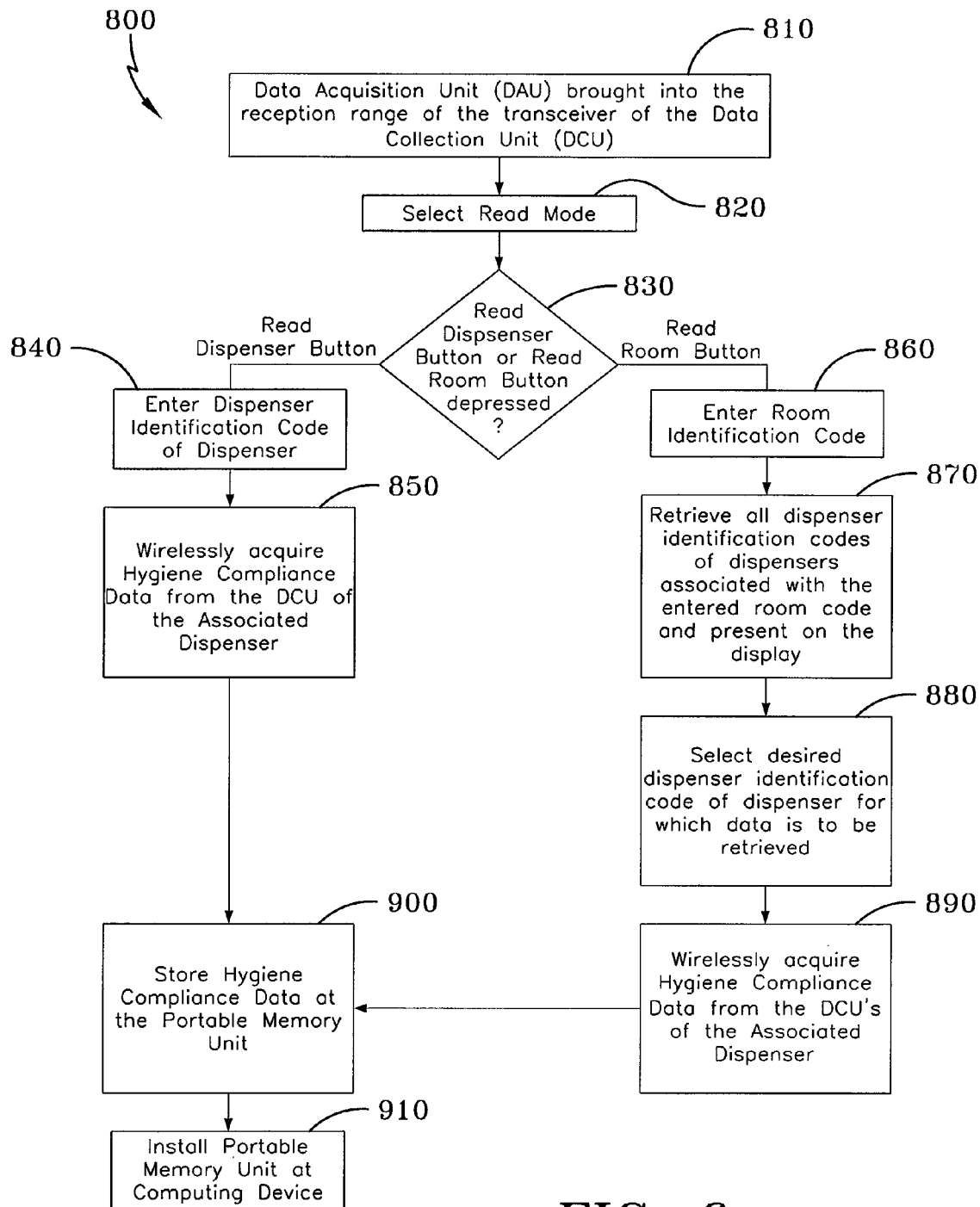
FIG. 6 shows a flow diagram of the operational steps taken to acquire collected hygiene compliance data from the data collection unit of one or more dispensers using the data acquisition unit in accordance with the concepts of the present invention.

After one or more dispensers 120 have been placed into operation, as discussed above, and have collected hygiene event data, one or more data acquisition units 160 are used to retrieve the event data in accordance with the operational steps generally referred to by the reference numeral 800, as shown in FIG. 6. Initially, to begin the acquisition of hygiene event data from the data collection unit 140, the data acquisition unit (DAU) 160 is moved into the communication range of the transceiver 320 of the data collection unit (DCU) 140, as indicated at step 810. Next, at step 820, the user selects the desired read mode using the keypad 430 of the data acquisition unit 160, whereupon the user can select from the read new, read all, and read/erase modes, as previously discussed. Continuing to step 830, the process determines whether the read dispenser button 450 or the read room button 460 has been depressed at the data acquisition unit 160. If the read dispenser button 450 is depressed, the process continues to step 840, where the user enters the dispenser identification code associated with the data collection unit 140 provided at the dispenser 120 of which the user desires to obtain hygiene event data. Continuing to step 850, the data acquisition unit 160 wirelessly acquires the hygiene event data from the data collection unit 140 of the associated dispenser 120. Alternatively, if at step 830 the user depresses the read room button 460, the process continues to step 860, whereupon the user enters or selects the room identification code that identifies a particular room with one or more dispensers installed therein, which contain hygiene event data to be acquired. Next, at step 870, the data acquisition unit 160 presents via the display 440 sequentially all of the dispenser identification codes of the dispensers 120 that are associated with the entered room code. As such, the user can select one or more dispenser identification codes of which hygiene event data is desired to be acquired or may select all the dispenser identification codes in which to acquire hygiene event data, as indicated at step 880. Once the desired dispenser identification codes have been selected for which hygiene event data is sought, the process continues to step 890, where the data acquisition unit 160 wirelessly acquires the hygiene event data from the data collection units 140 of the dispensers 120 with the selected dispenser identification codes. Once the hygiene event data has been acquired at either of steps 850 or 890, the process continues to step 900, where the hygiene compliance data is stored at the portable memory unit 170 of the data acquisition unit 160. Next, the portable memory unit 170 can then be removed from the data acquisition unit 160 and installed at the remote computing device 560, as indicated at step 910, to generate hygiene compliance reports, as previously discussed.

It will, therefore, be appreciated that one advantage of one or more embodiments of the present invention is that a hygiene event monitoring system provides a simple and user-friendly system in which to monitor activity at a dispenser. Another advantage of the present invention is that the hygiene event monitoring system allows a user to collect hygiene compliance data from a dispenser wirelessly at a substantial distance or range. Still another advantage of the present invention is that the hygiene event monitoring system in which data acquired from the data collection unit is stored on a portable memory unit that can be interfaced with a remote computing device to generate hygiene event reports.

Although the present invention has been described in considerable detail with reference to certain embodiments, other embodiments are possible. Therefore, the spirit and scope of the appended claims should not be limited to the description of the embodiments contained herein.

What is claimed is:

1. A hygiene compliance monitor for a dispenser maintaining material to be dispensed, said hygiene compliance monitor comprising:
   a dispenser controller that is coupled to an actuator to initiate the dispensement of material from the dispenser when said actuator is actuated;
   a data collection unit adapted to be coupled to said dispenser controller, said data collection unit including a data collection memory unit having a storage memory, such that the storage memory of said data collection unit is divided into a plurality of successive time segments of a predetermined time duration, wherein said data collection unit associates the number of actuations of said actuator with said time segment in which said actuations occurred; and
   a data acquisition unit in wireless communication with said data collection unit to receive the associated number of actuations and said time segments therefrom.

2. The hygiene compliance monitor of claim 1, wherein said actuator comprises a proximity sensor.

3. The hygiene compliance monitor of claim 1, wherein said data acquisition unit includes a data port adapted to receive a removable portable memory unit to store the number of actuations and associated time segments.

4. The hygiene compliance monitor of claim 1, wherein said wireless communication is encrypted.

5. The hygiene compliance monitor of claim 1, wherein said data collection unit identifies actuations of said actuator that are separated by about 3 seconds or less as a single dispensement.

6. The hygiene compliance monitor of claim 1, wherein said data collection unit is placed into a sleep mode until said data acquisition unit is within the communication range of said data collection unit.

7. The hygiene compliance monitor of claim 1, wherein said data collection unit identifies the time associated with the start and stop of each said time segment.

8. The hygiene compliance monitor of claim 1, wherein said data acquisition unit includes a user interface configured to set the duration of said at least one time segment.

9. The hygiene compliance monitor of claim 8, wherein said data collection unit is associated with a dispenser identification code, such that when said identification code is entered at said keypad, said data acquisition unit acquires the number of actuations and said associated time segments.

10. The hygiene compliance monitor of claim 9, wherein said data acquisition unit includes a set button that when engaged in a predetermined sequence within the communication range of said data collection unit assigns said dispenser identification code to said data collection unit.

11. The hygiene compliance monitor of claim 8, wherein said data acquisition unit includes a display and a data acquisition memory unit, such that said data acquisition memory unit maintains a database of at least one room identification code that is associated with at least one dispenser identification code, wherein when said room identification code is entered at said keypad, said display presents said at least one dispenser identification code associated with said room identification code.

12. The hygiene compliance monitor of claim 1, wherein said time segment is identified by a start time and an end time.

13. A hygiene compliance monitor for a dispenser maintaining material to be dispensed, said hygiene compliance monitor comprising:
a dispenser controller that is coupled to an actuator to initiate the dispensement of material from the dispenser when said actuator is actuated;
a data collection unit adapted to be coupled to said dispenser controller, said data collection unit including a data collection memory unit and an internal clock, said data collection memory unit having a storage memory divided into a plurality of successive time segments of a predetermined time duration, such that said data collection unit associates the number of actuations of said actuator with said time segment in which said actuations occurred, and wherein said data collection unit associates said at least one actuation of said actuator with a time stamp generated from said internal clock; and
a data acquisition unit in wireless communication with said data collection unit, wherein said data acquisition unit is configured to wirelessly set said clock and is further configured to receive at least one piece of data indicating the associated said time segment and said time stamp information of said at least one actuation.

14. A hygiene compliance monitor for a dispenser maintaining material to be dispensed, said hygiene compliance monitor comprising:
a dispenser controller that is coupled to an actuator to initiate the dispensement of material from the dispenser when said actuator is actuated;
a data collection unit adapted to be coupled to said dispenser controller, said data collection unit including a data collection memory unit having a storage memory, such that the storage memory of said data collection unit is divided into a plurality of successive time segments of a predetermined time duration, wherein said data collection unit associates the number of actuations of said actuator with said time segment in which said actuations occurred; and
a data acquisition unit in wireless communication with said data collection unit, wherein said data acquisition unit is configured to wirelessly program said data collection unit with location identifying information and is further configured to receive the data stored at said data collection unit.

15. A hygiene compliance system for a plurality of dispensers maintaining material to be dispensed, said hygiene compliance system comprising:
a plurality of hand hygiene compliance units, wherein each of said hand hygiene compliance units includes:
a dispenser controller coupled to an actuator to initiate the dispensement of material from a dispenser within the plurality of dispensers when said actuator is actuated; and
a data collection unit adapted to be coupled to said dispenser controller, said data collection unit including a data collection memory unit, said data collection memory unit having a storage memory, such that said storage memory of said data collection unit is divided into a plurality of successive time segments of a predetermined time duration, wherein said data collection unit associates the number of actuations of said actuator with said time segment in which said actuations occurred; and
a data acquisition unit in wireless communication with each said data collection unit within said plurality of hand hygiene compliance units, wherein said data acquisition unit is configured to wirelessly receive the data stored at each said data collection unit that are located within a predetermined proximity to one another nearly simultaneously.

16. A method of hygiene compliance monitoring comprising:
providing a data collection unit maintained by a dispenser, said dispenser including an actuator to initiate the dispensement of material from a refill container; wherein said data collection unit:
provides a storage memory;
divides said storage memory into a plurality of time segments of a predetermined duration;
monitors the actuation of said actuator;
associates the number of actuations of said actuator with the time segment in which said actuations occurred; and
stores the number of actuations and associated time segment at said storage memory;
providing a data acquisition unit having a portable memory unit, said data acquisition unit configured to wirelessly communicate with said data collection unit; and
transferring the number of actuations and associated time segments to said portable memory unit.

17. The method of claim 16 further comprising:
identifying the start and stop time of each said time segment.

18. The method of claim 17, further comprising:
removing said portable memory unit from said data acquisition unit;
installing said portable memory unit at a remote computing device; and
generating a report based on the number of actuations and associated time segments stored at said portable memory unit.

19. A hygiene compliance monitor for a dispenser maintaining material to be dispensed, said hygiene compliance monitor comprising:
a dispenser controller that is coupled to an actuator to initiate the dispensement of material from the dispenser when said actuator is actuated;

a data collection unit adapted to be coupled to said dispenser controller, said data collection unit including a data collection memory unit having a storage memory, such that the storage memory of said data collection unit is divided into a plurality of time segments of a predetermined time duration, wherein said data collection unit associates the number of actuations of said actuator with said time segment in which said actuations occurred; and a data acquisition unit in wireless communication with said data collection unit to receive the associated number of actuations and said time segments therefrom.

20. A hygiene compliance monitor for a dispenser maintaining material to be dispensed, said hygiene compliance monitor comprising:

a dispenser controller that is coupled to an actuator to initiate the dispensement of material from the dispenser when said actuator is actuated;

a data collection unit adapted to be coupled to said dispenser controller, said data collection unit including a data collection memory unit having a storage memory, such that data is stored within the storage memory of said data collection unit and said data is divided into a plurality of time segments of a predetermined time duration, wherein said data collection unit associates the number of actuations of said actuator with said time segment in which said actuations occurred; and a data acquisition unit in wireless communication with said data collection unit to receive the associated number of actuations and said time segments therefrom.

* * * * *